(12) United States Patent
Karmali

(10) Patent No.: US 8,415,388 B2
(45) Date of Patent: Apr. 9, 2013

(54) PHARMACEUTICAL COMPOSITIONS CONTAINING PACLITAXEL OROTATE

(75) Inventor: Rashida A. Karmali, Brooklyn, NY (US)

(73) Assignee: Savvipharm Inc., New York, NY (US)

( * ) Notice: Subject to any disclaimer, the term of this patent is extended or adjusted under 35 U.S.C. 154(b) by 207 days.

(21) Appl. No.: 13/066,793

(22) Filed: Apr. 25, 2011

(65) Prior Publication Data
US 2012/0197017 A1 Aug. 2, 2012

Related U.S. Application Data

(63) Continuation-in-part of application No. 11/063,943, filed on Feb. 22, 2005, now Pat. No. 8,034,823.

(51) Int. Cl.
*A61K 31/335* (2006.01)
*C07D 305/14* (2006.01)

(52) U.S. Cl.
USPC .......................................... 514/449; 549/510

(58) Field of Classification Search ........................ None
See application file for complete search history.

(56) References Cited

U.S. PATENT DOCUMENTS

| 5,916,596 A | 6/1999 | Desai et al. |
| 6,395,770 B1 | 5/2002 | Broder et al. |
| 6,730,698 B2 | 5/2004 | Broder et al. |

OTHER PUBLICATIONS

M.Stenger, Community Onc 2: 214-216 (2005).
L Hess et al Gynecol Oncol 17(2) 260-265 (2007).
R. Kunstfeld et al J. Inves Dermatol 120: 476-482 (2003).

*Primary Examiner* — James D Anderson
(74) *Attorney, Agent, or Firm* — Rashida A. Karmali

(57) ABSTRACT

This invention is related to orotic acid compounds of taxane cytotoxic agents and in particular to the conversion of the taxanes to their orotate esters. More particularly the pharmaceutical compositions of paclitaxel orotate and docetaxel orotate provide a strategy to minimize body weight loss during primary chemotherapy and improve patient outcomes and quality of life.

2 Claims, 6 Drawing Sheets

Orotic esters of Paclitaxel

PHARMACEUTICAL COMPOSITIONS CONTAINING PACLITAXEL OROTATE

CROSS-REFERENCE TO OTHER APPLICATION

This application is a Continuation-in-part of U.S. patent application Ser. No. 11/063,943 filed on Feb. 22, 2005, now U.S. Pat. No. 8,034,823 which is incorporated herein, with references in its entirety.

FIELD OF INVENTION

This invention is related to orotic acid compounds of taxane cytotoxic agents and in particular to the conversion of the taxanes to their orotate compounds to minimize body weight loss which is a surrogate for body reaction to the cytotoxic agent and may predict quality of life and clinical outcome.

BACKGROUND TO THE INVENTION

One of the important classes of cytotoxic agents is the taxanes which include paclitaxel, its derivatives and analogs. This invention relates to methods and compositions of taxane orotates that prevent or inhibit the body weight loss when taxanes are used in the treatment of cancers. Paclitaxel belongs to a class of chemotherapy drugs called plant alkaloids. The taxanes are made from the bark of the Pacific Yew tree (taxus). Paclitaxels has been approved for clinical use in the treatment of refractory ovarian cancer. It is effective for chemotherapy for several types of cancers including breast and has been approved for treatment of breast cancer as well. It is a candidate for treatment of cancers in the skin, lung cancer, head and neck cancer, bladder cancer, prostate cancer, esophageal cancer, polycystic kidney disease and malaria.

Paclitaxel is only slightly soluble in water and thus has created significant problems in developing suitable injectable and infusion formulations of paclitaxel for iv infusion using Cremophor EL™ (polyethoxylated castor oils) as drug carrier. Cremophor EL™ however, when administered intravenously, is itself toxic and prodices vasodilation, labored breathing, lethargy, hypotension and death in dogs.

To circumvent serious side effects of paclitaxel, paclitaxel is encapsulated in liposomes and microparticulate lipoidal vesicles. Paclitaxel encapsulated in cationic liposomes carries paclitaxel to blood vessels and thereby provides antiangiogenic effects. Paclitaxel encapsulated in liposomes prevented melanoma growth and invasiveness and improved survival in mice. In contrast, equimolar concentrations of paclitaxel solubilized in Cremophor EL™ had only insignificant effects on tumor growth in vivo. R. Kunstfeld et al, J. Inves Dermatol, 2003, 120:476-482.

Another formulation of paclitaxel available is Abraxane® or nab paclitaxel. It is paclitaxel bound to albumin in the form of nanoparticles. It is Cremophor EL™ free and is designed to reduce adverse reactions associate with Cremophor EL™ use. U.S. Pat. No. 5,916,596, issued Jun. 29, 1999 to Desai N P et al; U.S. Pat. No. 6,395,770, issued May 28, 2002 to Broder S et al.; U.S. Pat. No. 6,730,698, issued May, 4, 2004 to Broder S et al.; and M. Stenger, Community Oncology 2: 214-215 (2005)

Other taxanes include docetaxel (N-debenzoyl-N-tert-butoxycarbonyl-10-deacyl pactitaxel) has become commercially available as Taxotere® in parenteral form for treatment of breast cancer. The Chemotherapy Source Book, ed M. C. Perry, Lippincott Williams & Wilkins, $3^{rd}$ ed. 2001.

Great hopes have centered on the use of nanoparticles that are suitable for parenteral administration in aqueous suspension. This form of delivery obviates the need for administration of substantially water insoluble pharmacological agents (e.g., paclitaxel) in an emulsion containing for example, ethanol and polyethoxylated castor oil, diluted in saline because of the disadvantage of such known compositions is their propensity to produce side effects. Instead nanoparticles are prepared by a solvent evaporation technique from an oil-in-water emulsion under conditions of high shear forces by using human serum albumin as a stabilizing agent. Nevertheless, treatment related toxicities for sensory neuropathy, neutropenia, nausea, diarrhea and anorexia persist even with nab paclitaxel.

Obesity is implicated as a risk factor in the incidence and mortality due to cancer. However, there remains little or conflicting evidence about body weight changes, and specifically body weight loss due to side effects of cytotoxic agents, because of confounding variables. However, there is some evidence that a decrease in body weight during chemotherapy could potentially impact survival of cancer patients. Clearly there is need for chemical modification of paclitaxel molecule, regardless of whatever type of formulation it is administered as, for example i) in emulsion containing for example, ethanol and polyethoxylated castor oil, diluted in saline, ii) encapsulated in liposomes and microparticulate lipoidal vesicle, or iii) Abraxane® or nab paclitaxel which is paclitaxel bound to albumin in the form of nanoparticles.

The present invention related to orotates of taxane cytotoxic agents and in particular to methods of conversion of the taxanes to their orotate compounds to prevent or inhibit their toxic side effects, including body weight loss. Body weight loss during chemotherapy has been found in ovarian cancer to be a surrogate for body reaction to the cytotoxic agent and may predict quality of life and clinical outcome (Hess, L. M. et al., Gynecol Oncol. 2007, 107(2): 260-265).

Weight Change During Chemotherapy—Change of body weight during chemotherapy was found to be a strong factor for overall survival in ovarian cancer patients. Specifically, it was found that loss of body weight during primary therapy was an indicator for poor overall survival. In other words, weight gain was an indicator for improved survival. The chemotherapeutic agents studied in the retrospective study involving 792 advanced ovarian cancer patients were platinum and paclitaxel.

However, paclitaxel is also used in the treatment of breast cancer, non-small cell and small cell lung cancer, head and neck cancer, esophageal cancer, prostate cancer, bladder cancer and AIDS-related Kaposi's sarcoma. Thus there is a great need for safer formulations of paclitaxel which give a better rate of response, a wider spectrum of response, and/or reduce weight loss during chemotherapy. In particular, orotate compounds of paclitaxel and other taxanes may provide options for using improved formulations of paclitaxel.

The present invention is distinguishable from the prior art references described above because none of the prior art addresses the issue of preventing and/or reducing the body weight loss during chemotherapy, while maintaining the antitumor activity, as a strategy to reduce the toxicity and adverse drug reactions. More effective and less toxic taxanes orotates are widely sought and are a fundamental object of the invention. The pertinent subject matter of the above references is specifically incorporated herein by reference.

SUMMARY OF THE INVENTION

The present invention seeks to overcome drawbacks inherent in the prior art by providing compositions of taxane orotates that display reduced drug toxicity, and in particular prevent or inhibit body weight loss during the course of chemotherapy, when compared with taxanes.

This invention is in the field of chemical restructuring of pharmaceutical agents known to cause toxicity as a side effect, by producing their orotate esters. More particularly, it concerns orotate esters of taxanes—paclitaxel and docetaxel and analogs.

In view of the foregoing state of the art, the inventor has designed paclitaxel orotate that retains its tumor inhibiting activity but inhibits body weight loss during the period chemotherapy is given. FIG. 1.

A principle objective of the invention is to obtain a composition of paclitaxel orotate in order to reduce the toxicity of paclitaxel which is related to causing body weight loss during chemotherapy.

The invention also specifically provides a process for the preparation of paclitaxel orotate starting paclitaxel in DMF, orotic acid and imidazole. The process comprises reacting taxol with orotic acid and imidazole at room temperature, collecting the paclitaxel mono ester and purifying it by HPLC.

DETAILED DESCRIPTION OF THE INVENTION

Figure 1:
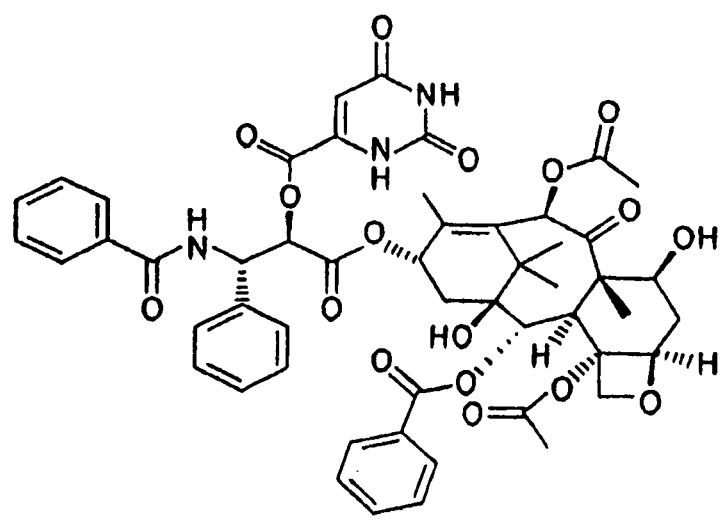
FIG. 1 illustrates the structures of paclitaxel orotate ester.

Taxane based cancer therapy regimens are broadly used in the treatment of ovarian, breast cancer, non-small cell and small cell lung cancer, head and neck cancer, esophageal cancer, prostate cancer, bladder cancer and AIDS-related Kaposi's sarcoma. Taxanes, which include paclitaxel, docetaxel and their analogs, are antimicrotubule agents, inhibit microtubule structures within the cell and ultimately cause cell death. Specifically, taxanes such as paclitaxel bind and stabilize microtubules, cause cells to arrest in mitosis and result in cytostatic or cytotoxic responses. E. Chu, et al., ed Cancer Chemotherapy Drug Manual (2010) Jones and Bartlette Publishers.

Paclitaxel (commercial names: Taxol, Anzatax, Paxene) (chemical name: β (Benzoylamino-α-hydroxy-benzenepropanoic acid, 6,12b-bis(acetyloxy)-12(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca[3,4]benz[1,2-b]oxet-9-ylester,[2aR-[2aα,4β,4aβ,6β,9α,(αR*,βS), 11α, 12α, 12aα, 12bα]]), has a molecular weight of 853.9.

The high molecular weight bulky structure and main hepatic metabolism of the taxanes renders them idea candidates for intra cavitary administration. However, abdominal pain precludes the administration of paclitaxel doses above 125 mg per m$^2$, intraperitoneally. Systemic toxicity is mild at doses of 100 mg per m$^2$. Oral bioavailability of paclitaxel is poor but relevant concentrations are achieved if the taxanes are administered orally after treatment with cyclosporine. U.S. Pat. No. 6,730,698, issued May 4, 2004 to Broder S. et al.

The most impressive clinical results of paclitaxel have been seen in patients with ovarian and breast cancer. Its use in combination with a platinum compound as primary induction therapy in suboptimally debulked stage III or IV ovatrian cancer, as a component of adjuvant chemotherapy after primary local treatment, is associated with a clear survival advantage in phase III studies. Paclitaxel has also received regulatory approval for the second-line treatment of Kaposi's sarcoma associated with the acquired immunodeficiency syndrome, in combination with cisplatin as primary treatment of non-small cell lung cancer, and as a component of adjuvant chemotherapy in the high-risk-node-positive breast cancer.

Docetaxel (commercial name: Taxotere) (chemical name: 4-acetoxy-2α-benzoyloxy-5β,20-epoxy-1,7β,10β-trihydroxy-9-oxotax-11-ene-13α-yl-(2R,3S)-3-tert-butoxycarbonylamino-2-hydroxy-3-phenylpropionate), has a molecular weight of 807.9. It is metabolized in the liver and its toxicities include neutropenia, hypersensitivity, fluid retention, skin rash, neurosensory and cardiovascular.

Drug therapies that are used for the treatment of patients with cancer can damage a number of organs and organ systems. Among those most frequently damaged are tissues with rapid cell turnover, such as the hematopoetic system, the gastrointestinal tract, and the genitourinary tract. The heart, made up of tissue without rapid cell turnover and therefore incapable of rapid recovery, is occasionally affected by chemotherapy. Because the cardiac effects of such therapy may be disabling or life threatening, it may necessitate a major modification of treatment to prevent cardiac toxicity. In some instances the effects of the chemotherapeutic drugs on the heart are self-limited and readily reversible with the withdrawal of the offending agent. However, in others the damage may be devastating, progressive, irreversible and ultimately fatal. Some forms of cardiotoxicity are poorly predictable and may affect patients without warning, sometimes during the first exposure. In other setting the toxicity is well defined and readily predictable. Yet there is considerable variation in the exposure needed to achieve similar levels of tissue damage.

Some drugs are toxic by themselves, but their toxicity may be potentiated when they are used in combination with other agents, the combination may be more toxic than the sum of the toxicities of the individual components. As it is necessary to achieve the greatest antitumor potential of the drug while keeping end-organ toxicity at an acceptable level, the evaluation of patients treated with toxic drugs must be individualized.

Paclitaxel causes neutropenia, peripheral neuropathy, transient myalgia, gastrointestinal effects such as vomiting and cardiac rhythm disturbances. Little is known about the incidence of weight change among ovarian cancer patients. Women who are diagnosed and treated with ovarian cancer are known to experience a variety of chemotherapy related side effects than can affect quality of life. Ovarian cancer patients may experience cachexia as a result of advanced disease and therefore suffer loss of body weight. Weight loss also occurs after surgery by is regained gradually over the year following surgery and tends to be body fat and not muscle mass. However, it was unclear how an increase or decrease in body weight during chemotherapy could impact survival. Therefore, Less, L. M., et al, Gynecol. Oncol. 2007, 107:260-265, undertook a retrospective data review of 792 advanced ovarian cancer patients who participated in a phase III randomized trial of paclitaxel/cisplatin versus paclitaxel/carboplatin. Results obtained indicated that change in body weight during primary chemotherapy was a prognostic factor for overall survival, that is loss of body weight during primary therapy was an indicator of poor overall survival. In other words, weight gain was an indicator of improved survival and the study conclude that strategies to minimize weight loss during primary chemotherapy should be developed to improve patient outcomes.

It is an objective of the present invention to minimize weight loss during paclitaxel chemotherapy by using paclitaxel orotate.

The present invention provides a method to minimize body weight loss during chemotherapy with paclitaxel orotate in human ovarian cancer.

Methods of Reducing Side Effects of an Agent by Converting it to an Orotate Derivative.

In an application Ser. No. 11/063,943, filed Feb. 22, 2005 the inventor described the methods of increasing the oral bioavailability of pharmaceutical agents that are poorly absorbed from the gastrointestinal tract by converting them into orotate salts. The inventor described a reduction in organ levels of drugs given as orotate salts, compared with the pharmaceutical form of the drug, thus reducing the potential for toxicity at the time of drug administration and in the long term after the primary cancer or disease is cured. Therefore, an especially useful formulation of the orotate salt of the pharmaceutical agent can provide rapid onset and consistent action using orotate salts and reduce drug interactions and side-effects. All cited references are incorporated herein fully.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the synthesis of UMP. Biochemistry, ed Lubert Stryer, ed, W.H. Freeman & Co NY, 4$^{th}$ ed, 739-762 (1995). It has also been reported that 5-Fluorouracil is toxic to the liver, as measured by incorporation in the acid soluble fraction, RNA and DNA in normal tissues in the liver of rats. Orotic acid administration decreased the incorporation into the liver and intestinal RNA, thus suggesting that it reduces 5-FU induced toxicity in the liver. El Hag I A et al, In vivo 1: 309-312 (1987). The present invention provides drug orotate derivatives that under go dissolution to release the drug as a charged molecule and free orotic acid, which in turn reduces drug-induced liver, heart or other tissue toxicity.

The present invention provides methods and compositions to increase the effectiveness of a pharmaceutical agent by converting said pharmaceutical agent to an orotate composition and, administering said orotate ester to a subject in need thereof, said pharmaceutical agent selected from the group of consisting of paclitaxel and docetaxel.

The invention provides methods and compositions to improve patient outcomes by minimizing weight loss during primary chemotherapy.

EXAMPLES

Example 1

Figure 2:
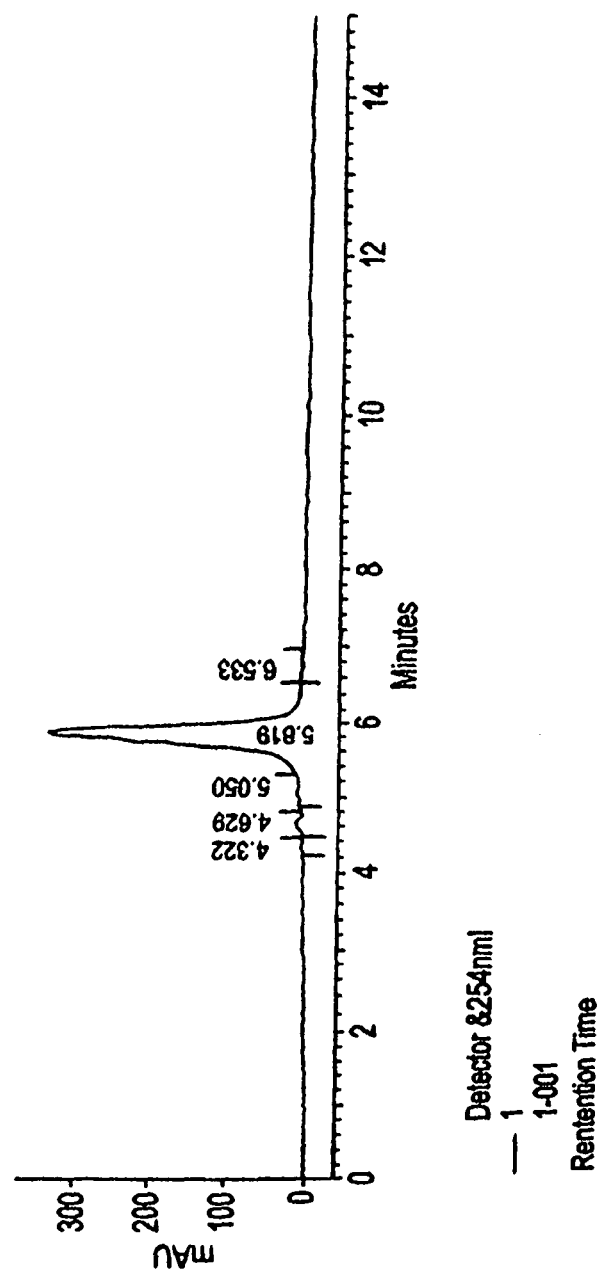
FIG. 2 illustrates the purification of paclitaxel orotate by HPLC
FIG. 3 Mass Spectrograph illustrating paclitaxel orotate
FIG. 4 NMR illustrating paclitaxel orotate

Chemical Synthesis of Paclitaxel Orotate 1 eq of paclitaxel made in DMF was treated with 1.1 eq orotic chloride/imidazole at room temperature. The mixture was stirred overnight. The mixture was filtered and the solid residue was purified on a column. This was followed by preparative HPLC to obtain a colorless solid of paclitaxel orotate mono ester. FIG. 2. During the purification processes protic solvents such as methanol and water should be avoided.

Figure 3:
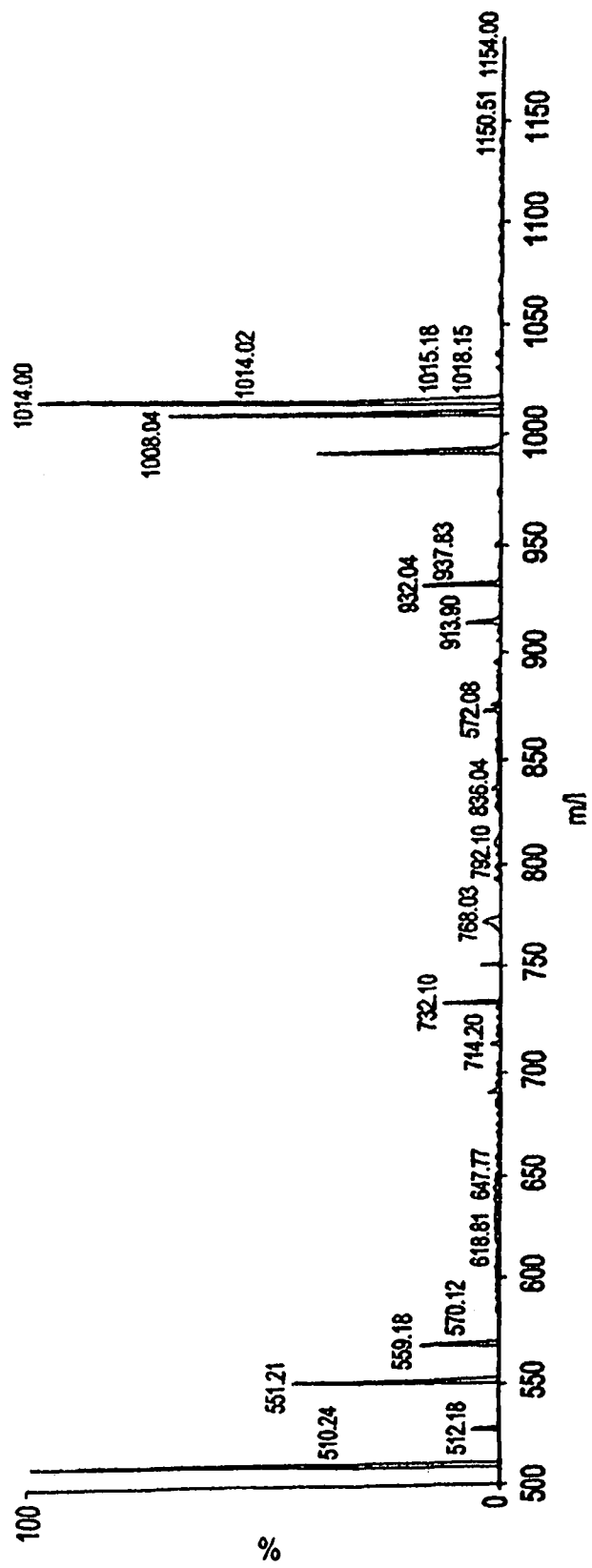
Figure 4:
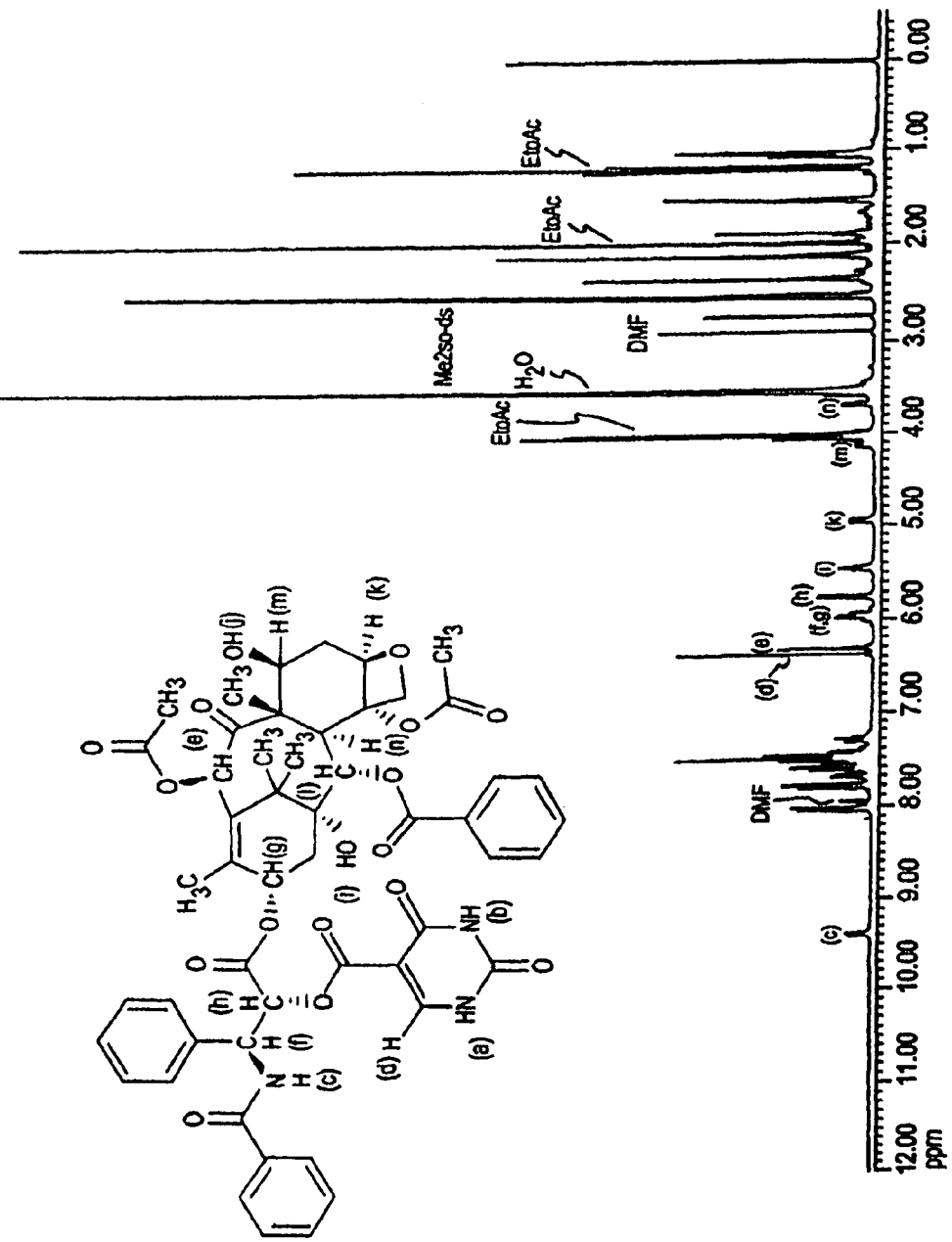

The sample was prepared in acetonitrile to avoid decomposition, for analysis by Mass Spectroscopy. FIG. 3. Analysis by Nuclear Magnetic Resonance FIG. 4 indicates that the structure is paxlitaxel orototate mono ester.

Example 2

Response of OVCAR-5 Human Ovarian Tumor to Treatment with Paclitaxel and Paclitaxel Orotate The purpose of the experiment was to evaluate the antitumor efficacy of paclitaxel and paclitaxel orotate mono ester against subcutaneously (SC) implanted human OVCAR-5 ovarian tumor xenografts in female six week old athymic NCr-nu/nu mice.

Drug formulation—A 2.32 mg/mL solution of paclitaxel orotate (referred to as "paclitaxel orot" was formulated on each day of treatment by adding 100% ethanol to the powder first and vortexing the vial and sonicating for 10-20 sec until a solution was achieved. Then an equal volume of cremophor EL was added and finally, saline was added to yield a concentration of 2.32 mg/mL in 12.5% cremophor EL/12.5% ethanol/75% saline. A portion of the 2.32 mg/mL solution was further diluted with the complete vehicle to 1.16 mg/mL. Dosing solutions were stored at room temperature between formulation and administration and were injected within 4 h of formulation.

An 8.0 mg/mL stock solution of paclitaxel (Cedarburg Hauser, Boulder, Colo.; lot no. Tech 6 00600-A) in 50 cremophor EL/50% ethanol was formulated on the first day of treatment and stored at 4° C. On each day of treatment, a portion of the 8.0 mg/mL stock solution was diluted with saline to yield a concentration of 2.0 mg/mL in 12.5% cremophor EL/12.5% ethanol/75% saline. The dosing solution of paclitaxel was administered within 20 minutes of the dilution of the 8.0 mg/mL stock solution and was kept on warm water until injected. A portion of the 2.0 mg/mL solution was further diluted with the complete vehicle to 1.0 mg/mL. The 1.0 mg/mL solution was stored at room temperature between formulation and administration. Cremophor® EL was purchased from Sigma-Aldrich, Inc. (St. Louis, Mo.; batch #037K0213) and stored at room temperature. Ethanol (ethyl alcohol USP, 200 Proof) was purchased from Aaper Alcohol and Chemical Co. (Shelbyville, Ky., lot no. 07A0523) and stored at room temperature. Saline (Saline Solution 0.9%, for animal use only) was purchased from Phoenix Pharmaceutical, Inc. (St. Joseph, Mo., lot no. 710367F) and stored at room temperature. During the formulation period, saline was stored at 4° C. Paclitaxel orotate, paclitaxel, and the vehicles were administered to mice by exact individual animal's body weight on each day of treatment, with the injection volume being 0.1 mL/10 g body weight.

Five groups of 10 mice per group were used on Day 21. Animals in Group 1 were treated N with the paclitaxel and paclitaxel orotate vehicle (12.5% cremophor EL/12.5% ethanol/75% saline) on a Q2D×3/2 wks schedule, starting on Day 21 (Days 21, 23, 25, 28, 30, and 32). Animals in Groups 2 and 3 were treated IV with paclitaxel orotate at doses of 23.2 and 11.6 mg/kg/inj., respectively, on a Q2D×3/2 wks schedule. Animals in Groups 4 and 5 were treated IV with paclitaxel at doses of 20 and 10 mg/kg/inj., respectively, on a Q2D×3/2 wks schedule.

Tumors were measured and volume determined using formula $L \times W^2/2 = mm^3$; and weight calculated assuming 1 $mm^3 = 1$ mg. The study was terminated 63 days after tumor implantation Results:

Tumor weight—Administration of paclitaxel orotate IV at doses of 23.2 and 11.6 mg/kg/inj. (Groups 2 and 3, respectively) was tolerated without deaths and was associated with maximum mean body weight losses of 14% (3.6 g) and 5% (1.2 g), respectively, observed on Day 35. The body weights on Day 35 in both groups were not statistically significantly different from the body weights in the control group (Group 1 vs. Group 2: P=0.187; Group 1 vs. Group 3: P=0.826). The median tumor reached two tumor mass doublings in >42.0 (tumors of seven out often animals did not reach two tumor mass doublings by the day of study termination) and 23.0 days, producing a delay in the growth of the median tumor of >22.7 and 3.7 days, respectively. Growth of the tumors in both paclitaxel orotate-treated groups was found to be statistically different from the growth of the tumors in the control group, when individual animal's times to reach two tumor mass doublings were compared (Group 1 vs. Group 2: p<0.001; Group 1 vs. Group 35: P=0.029). The TIC values on Day 63 were 21% and 60%, respectively. While tumor weights on Day 63 in the group treated with paclitaxel orotate at a dose of 23.2 mg/kg/inj. was statistically different from the tumor, weights in the vehicles-treated control group (Group 1 vs. Group 2: P=0.003), tumor weights on Day 63 in the group treated with paclitaxel orotate at a dose of 11.6 mg/kg/inj. were not statistically different (Group 1 vs. Group 3: P=0.078). Response of the SC-implanted human OVCAR-5 ovarian tumor xenografts to the treatment with paclitaxel orotate is presented graphically in FIG. 5.

Figure 5:
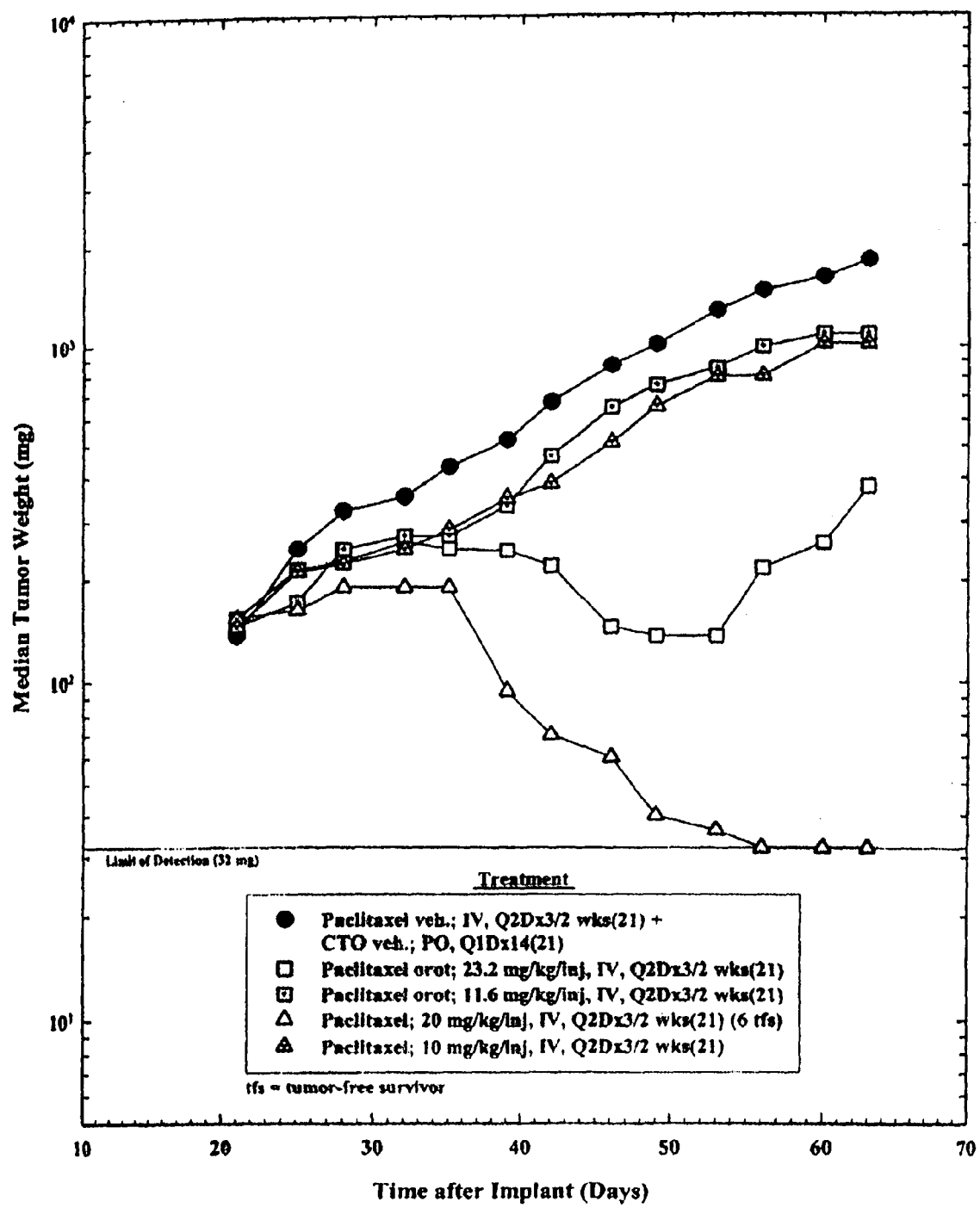
FIG. 5 illustrates the response of human Ovcar-5 ovarian tumor to treatment with paclitaxel orotate and paclitaxel

Administration of paclitaxel IV at a dose of 20 or 10 mg/kg/inj. plus CTO at a dose of 513 mg/kg/inj. (Groups 12 and 13, respectively) was tolerated without deaths and was associated with maximum mean body weight losses of 16% (4.0-4.1 g) and 12% (3.2 g), respectively, observed on Days 32 and 35. The median tumor reached two tumor mass doublings in >42.0 days (tumors of all ten animals did not reach two tumor mass doublings by the day of study termination) and 26.7 days, producing delays in the growth of the median tumor of >22.7 and 7.4 days, respectively. There were four tumor-free animals on Day 63 in the combination group in which paclitaxel was administered at a dose of 20 mg/kg/inj. The TIC values on Day 63 were 2% and 58%, respectively. Growth of the tumors in both combination groups was found to be statistically different from the growth of the tumors in the control group, when individual animal's times to reach two tumor mass doublings were compared (Group 1 vs. Group 12: P<0.001; Group 1 vs. Group 13: P=0.012). Only individual animals' tumor weights on Day 63 in the combination group in which paclitaxel was administered at a dose of 20 mg/kg/inj. Were statistically different from that of in the control group (Group 1 vs. Group 12: P<0.001; Group 1 vs. Group 13: P=0.109). Tumor growth in both combination groups was not different from the growth of the tumors in the group treated with a dose of paclitaxel of 20 mg/kg/inj. alone (Group 12 vs. Group 10: individual animal's times to reach two tumor mass doublings—unevaluable due to all tumors not reaching two tumor mass doublings; individual animal's tumor weights on Day 63—P=0.516) or with a dose of 10 mg/kg/inj. alone (Group 13 vs. Group 11: individual animal's times to reach two tumor mass doublings—P=0.887; individual animal's tumor weights on Day 63—P=0.869). FIG. 5.

Treatment with paclitaxel orotate alone at a dose of 23.2 or 11.6 mg/kg/inj. (Groups 4 and 5, respectively) did not result in a greater antitumor activity than the treatment with paclitaxel alone at a dose of 20 or 10 mg/kg/inj. (Groups 10 and 11, respectively) when individual animal's times to reach two tumor mass doublings were compared (Group 4 vs. Group 10: P=0.067; Group 5 vs. Group 11: P=0.385).

Effect of Chemotherapy with Paclitaxel Orotate and Paclitaxel on Body Weight.

Figure 6:
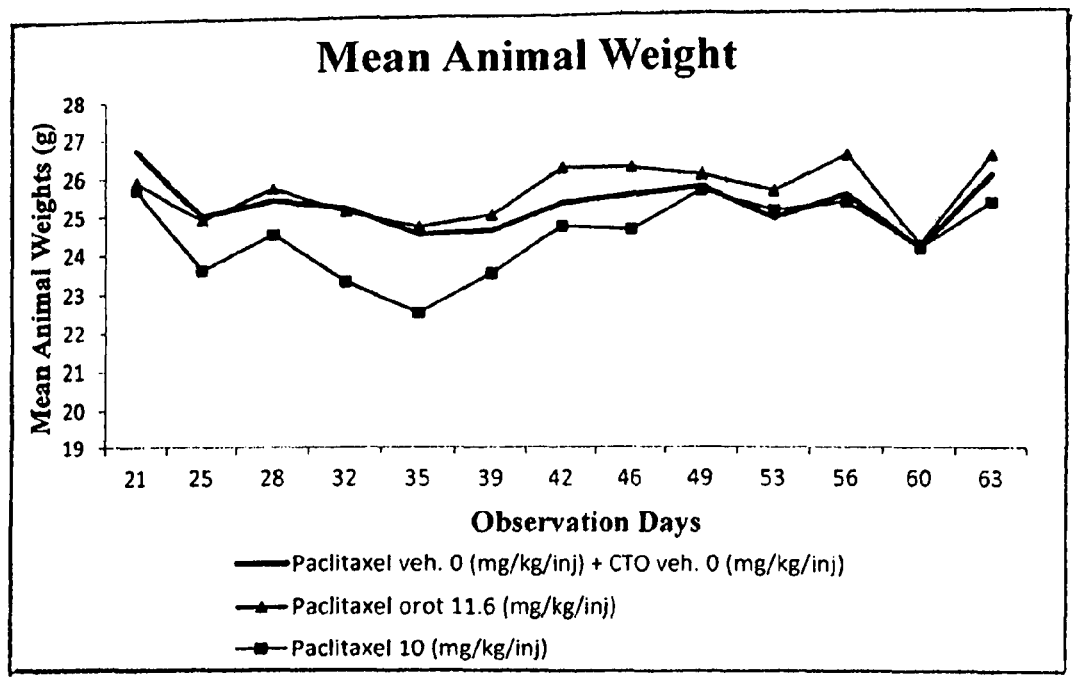
FIG. 6 illustrates the response on body weight due to treatment with low dose of paclitaxel orotate and paclitaxel
Figure 7:
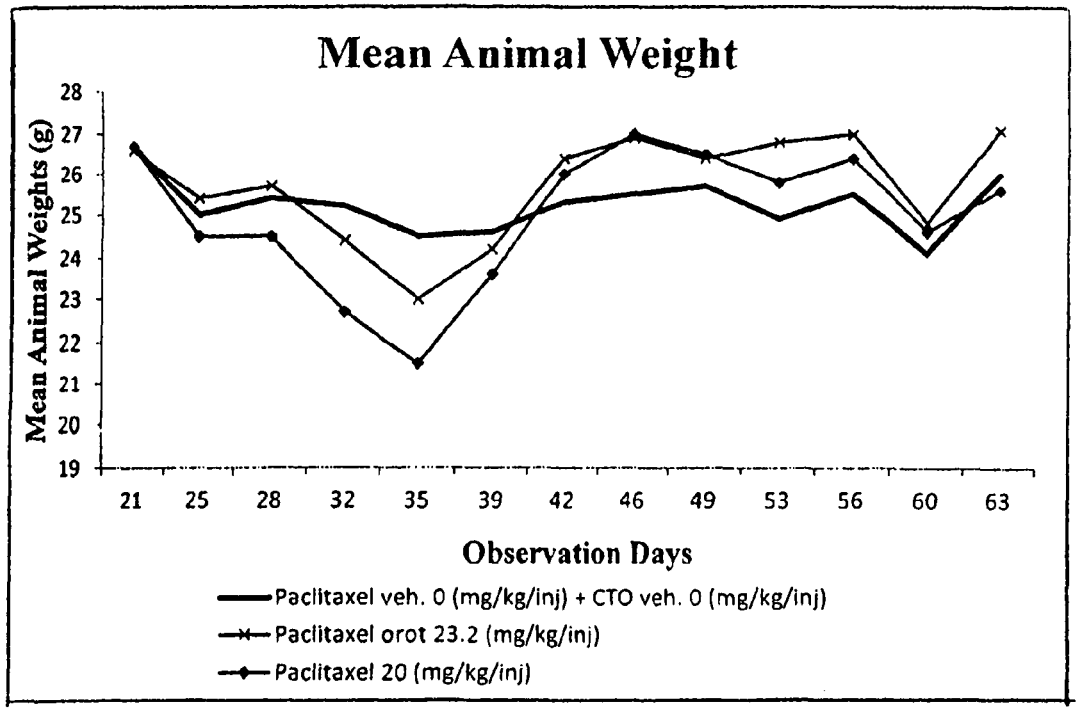
FIG. 7 illustrates the response on body weight due to treatment with high dose of paclitaxel or paclitaxel orotate

The body weights on Day 35 in the groups treated with paclitaxel orotate were not statistically different from control. However, in the groups treated with paclitaxel at the equivalent doses, the body weights were statistically significantly different between the group treated with 20 mg/kg/inj compared with control (Group 4 vs. Group 1: P=0.01). Change in mean body weights over the course of the experiment in paclitaxel orotate-treated and paclitaxel-treated groups is presented graphically in FIG. 6 and FIG. 7. These unexpected results on the effect of paclitaxel orotate in minimizing body weight loss provide an important strategy to minimize body weight loss in prospective clinical studies in which various formulations of taxanes like paclitaxel and docetaxel are used in chemotherapy to improve patient outcomes regardless of whether administered as, for example i) in emulsion containing ethanol and polyethoxylated castor oil, diluted in saline, ii) encapsulated in liposomes and microparticulate lipoidal vesicle, or iii) Abraxane® or nab paclitaxel which is paclitaxel bound to albumin in the form of nanoparticles.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:
1. A composition comprising paclitaxel orotate.
2. A compound of the formula:

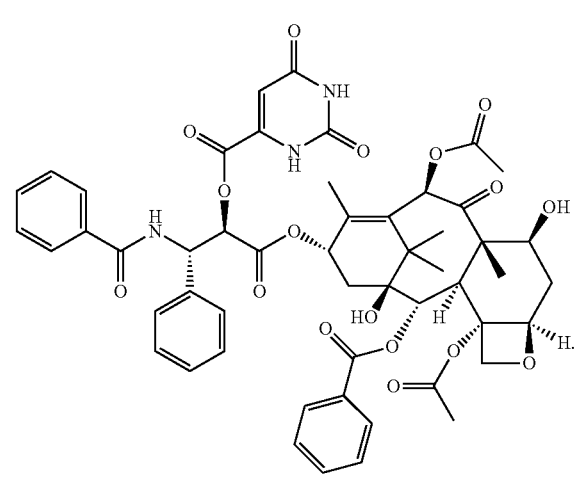

* * * * *